(12) United States Patent
Kistler et al.

(10) Patent No.: US 7,332,179 B2
(45) Date of Patent: Feb. 19, 2008

(54) TISSUE PRODUCTS COMPRISING A CLEANSING COMPOSITION

(75) Inventors: Annastacia Kistler, Appleton, WI (US); David M. Koenig, Menasha, WI (US); Duane G. Krzysik, Appleton, WI (US); Corey Cunningham, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 752 days.

(21) Appl. No.: 10/735,591

(22) Filed: Dec. 12, 2003

(65) Prior Publication Data

US 2005/0129741 A1    Jun. 16, 2005

(51) Int. Cl.
*A61F 13/00*    (2006.01)
(52) U.S. Cl. .................................................. 424/443
(58) Field of Classification Search ............ 424/70.13, 424/70.16, 70.11, 70.12, 400, 443
See application file for complete search history.

(56) References Cited

U.S. PATENT DOCUMENTS

| | | | |
|---|---|---|---|
| 2,216,522 A | 10/1940 | Sanders |
| 2,450,919 A | 10/1948 | Runnels |
| 3,301,746 A | 1/1967 | Sanford et al. |
| 3,567,118 A | 3/1971 | Shephard et al. |
| 3,812,000 A | 5/1974 | Salvucci |
| 3,814,101 A | 6/1974 | Kozak |
| 3,875,942 A | 4/1975 | Roberts et al. |
| 3,974,025 A | 8/1976 | Ayers |
| 4,191,609 A | 3/1980 | Trokhan |
| 4,208,459 A | 6/1980 | Becker et al. |
| 4,295,976 A | 10/1981 | Dessaint |
| 4,382,919 A | 5/1983 | Alonso et al. |
| 4,425,128 A | 1/1984 | Motomura |
| 4,637,859 A | 1/1987 | Trokhan |
| 4,650,470 A | 3/1987 | Epstein |
| 4,753,643 A | 6/1988 | Kassai |
| 4,790,836 A | 12/1988 | Brecher |
| 4,817,790 A | 4/1989 | Porat et al. |
| 4,917,134 A | 4/1990 | Simonzi et al. |
| 5,068,225 A | 11/1991 | Pennell |
| 5,134,229 A | 7/1992 | Saferstein |
| 5,216,057 A | 6/1993 | Pratt |
| 5,505,943 A | 4/1996 | Fortney |
| 5,591,498 A | 1/1997 | Arakawa |
| 5,597,567 A | 1/1997 | Whitcup |
| 5,641,783 A | 6/1997 | Klein |
| 5,646,178 A | 7/1997 | Walker |
| 5,648,083 A | 7/1997 | Blieszner et al. |
| 5,649,921 A | 7/1997 | Arakawa et al. |
| 5,679,658 A | 10/1997 | Elson |
| 5,785,993 A | 7/1998 | Baker |
| 5,791,352 A | 8/1998 | Reich |
| 5,867,839 A | 2/1999 | Hegoas et al. |
| 6,013,679 A | 1/2000 | Kuo |
| 6,030,995 A | 2/2000 | Shayman |
| 6,083,854 A | 7/2000 | Bogdanski et al. |
| 6,096,382 A | 8/2000 | Gueret |
| 6,133,325 A | 10/2000 | Schwartz |
| 6,178,922 B1 | 1/2001 | Denesuk |
| 6,303,125 B1 | 10/2001 | Ofek |
| 6,337,066 B1 | 1/2002 | Jacquier |
| 6,340,664 B1 | 1/2002 | Gassenmeier |
| 6,407,141 B1 | 6/2002 | Hart |
| 6,436,481 B1 | 8/2002 | Chabracek |
| 6,440,471 B2 | 8/2002 | Walker |
| 6,486,140 B2 | 11/2002 | Hansson |
| 6,492,307 B1 | 12/2002 | Matsuo et al. |
| 6,500,539 B1 | 12/2002 | Chen |
| 6,565,640 B1 | 5/2003 | Bengs et al. |
| 6,569,261 B1 | 5/2003 | Aubay et al. |
| 2002/0002357 A1 | 1/2002 | Suzuki |
| 2002/0015684 A1* | 2/2002 | Vatter ..................... 424/70.12 |

FOREIGN PATENT DOCUMENTS

| | | |
|---|---|---|
| EP | 0398891 B1 | 8/1992 |
| EP | 0510200 B1 | 10/1992 |
| EP | 0561489 A2 | 9/1993 |
| EP | 0443043 B1 | 4/1995 |
| EP | 0763341 A1 | 3/1997 |
| EP | 0626843 B1 | 10/1997 |
| EP | 0808151 B1 | 11/1997 |
| EP | 0792322 B1 | 5/1999 |
| EP | 0792323 B1 | 6/1999 |
| EP | 0992518 A1 | 4/2000 |
| EP | 1014938 | 7/2000 |
| EP | 1066852 A1 | 1/2001 |

(Continued)

OTHER PUBLICATIONS

Invitation to Pay Additional Fees from PCT/US2004/016936 dated Feb. 28, 2005.

(Continued)

*Primary Examiner*—Sharon Kennedy
(74) *Attorney, Agent, or Firm*—Armstrong Teasdale LLP

(57) ABSTRACT

The present invention discloses tissue products comprising a cleansing composition. The cleansing composition removes soil and contaminants from the skin's surface and comprises a thermoplastic polymer and a water soluble neutral oligosaccharide. In one embodiment, the cleansing composition comprises polymethylmethacrylate and a water soluble starch.

35 Claims, No Drawings

FOREIGN PATENT DOCUMENTS

| | | |
|---|---|---|
| EP | 0732110 B1 | 10/2001 |
| EP | 1152013 A1 | 11/2001 |
| EP | 0642351 B1 | 3/2002 |
| EP | 0831856 B1 | 8/2002 |
| EP | 1238949 A1 | 9/2002 |
| EP | 1241227 A1 | 9/2002 |
| EP | 0772446 B1 | 10/2002 |
| EP | 1245247 A1 | 10/2002 |
| EP | 1262200 A2 | 12/2002 |
| JP | 4-284237 | 10/1992 |
| JP | 7300425 | 11/1995 |
| JP | 8-019571 | 1/1996 |
| JP | 8-038547 | 2/1996 |
| JP | 2002-128892 A2 | 5/2002 |
| WO | WO 94/14472 | 7/1994 |
| WO | WO 95/26197 | 10/1995 |
| WO | WO 95/33467 | 12/1995 |
| WO | WO 96/37519 | 1/1996 |
| WO | WO 96/04003 | 2/1996 |
| WO | WO 96/24371 | 8/1996 |
| WO | WO 97/17085 | 5/1997 |
| WO | WO 97/18790 | 5/1997 |
| WO | WO 98/16104 | 4/1998 |
| WO | WO 98/53800 | 12/1998 |
| WO | WO 99/12541 | 3/1999 |
| WO | WO 00/17371 | 3/2000 |
| WO | WO 00/71139 | 11/2000 |
| WO | WO 01/01949 A1 | 1/2001 |
| WO | WO 01/05370 | 1/2001 |
| WO | WO 01/06973 | 2/2001 |
| WO | WO 01/83877 A1 | 11/2001 |
| WO | WO 02/05789 A2 | 1/2002 |
| WO | WO 02/05839 | 1/2002 |
| WO | WO 02/07746 | 1/2002 |
| WO | WO 02/94864 | 1/2002 |
| WO | WO 02/09792 | 2/2002 |
| WO | WO 03/084497 A1 | 10/2003 |
| WO | WO 2004/093833 A2 | 11/2004 |

OTHER PUBLICATIONS

Aniansson, et al., Anti-Adhesive Activity of Human Casein Against *Streptococcus pneumoniae* and *Haemophilus influenzae*, Microb. Path., 1990, pp. 315-323, vol. 8, No. 5.

Asakura, et al., Inhibition of Cell Adhesion by High Molecular Weight Kininogen, J. Cell. Biol., 1992, pp. 465-476, vol. 116, No. 2.

Barghouthi, et al., Inhibition of Dextran of *Pseudomonas aeruginosa* Adherence to Epithelial Cells, Am. J. Respir. Critical Care Med., 1996, pp. 1788-1793, vol. 154, No. 6 Part I.

Buckingham, et al., Etiological Factors in Diaper Dermatitis: The Role of Feces, Pediatric Dermatology, 1986, pp. 107-112, vol. 3, No. 2.

Calderone, et al., Adherence and Receptor Relationships of *Candida albicans*, Microb. Rev., 1991, pp. 1-20, vol. 55, No. 1.

Chiquet-Ehrismann, R., Anti-Adhesive Molecules of the Extracellular Matrix, Curr. Opin. Cell Biol., 1991, pp. 800-804, vol. 3, No. 5.

Chiu, et al., Adherence of *Burkholderia cepacia* to Respiratory Tract Epithelial Cells and Inhibition with Dextran, Microb., 2001, pp. 2651-2658, vol. 147, No. 10.

Davey, et al., Variable Selection and Multivariate Methods for the Identification of Microorganisms by Flow Cytometry, Cytometry, 1996, pp. 162-168, vol. 35.

Draser, et al., Intestinal Microbiology: Aspects of Microbiology, Am. Soc. For Microbiol., 1985.

Feng, et al., Improved Clearability of Cystic Fibrosis Sputum with Dextran Treatment in Vitro, Am. J. Respir. Critical Care Med., 1998, pp. 710-714, vol. 157, No. 3, Part 1.

Guzman-Murillo, et al., Anti-Adhesive Activity of Sulphated Exopolysaccharides of Microalgae on Attachment of Red Sore Disease-Associated Bacteria and *Helicobacter pylori* to Tissue Culture Cells, Lett. Appl. Microbiol., 2000, pp. 473-478, vol. 30, No. 6.

Hostetter, M., Adhesins and Ligands Involved in the Interaction of *Candida* Spp. with Epithelial and Endothelial Surfaces, Clinical Microbiol. Rev., 1994, pp. 29-42, vol. 7, No. 1.

Kelly, et al., Anti-adhesive Strategies in the Prevention of Infectious Disease at Mucosal Surfaces, Expert Opin. Investig. Drugs, 2000, pp. 1711-1721, vol. 9, No. 8.

Khaled, et al., Multiple Mechanisms May Contribute to the Cellular Anti-Adhesive Effects of Phosphorothioate Oligodeoxynucleotides, Nucleic Acids Res., 1996, pp. 737-745, vol. 24, No. 4.

Kozai, et al., In Vitro Study of Antibacterial and Anti-Adhesive Activities Of Fluoride-Containing Light-Cured Fissure Sealants and a Glass Ionomer Liner/Base Against Oral Bacteria, ASDC J. Dent. Child, 2000, pp. 117-122, 182-3, vol. 67, No. 2.

Lundmark, et al., Perlecan Inhibits Smooth Muscle Cell Adesion to Fibronectin: Role of Heparan Sulfate, J. Cell Physiol., 2001, pp. 67-74, vol. 188, No. 1.

Mannucci, et al., Beta-Benzal-Butyric Acid: A New Anti-Adhesive Drug, Acta Univ. Carol Med. Monogr., 1972, pp. 409-412, vol. 53.

Morra, et al., Non-Fouling Properties of Polysaccharide-Coated Surfaces, J. Biomater. Sci. Polym. Ed., 1999, pp. 1107-1124, vol. 10, No. 10.

Pavesio, et al., Anti-Adhesive Surfaces Through Hyaluronan Coatings, Med. Device Technol., 1997, pp. 20-21, 24-27, vol. 8, No. 7.

Portoles, et al., Poloxamer 407 as a Bacterial Adhesive for Hydrogel Contact Lenses, J. Biomed. Mater. Res., 1994, pp. 303-309, vol. 28, No. 3.

Robbins, R.C., Flavones in Citrus Exhibit Anti-Adhesive Action on Platelets, Int. J. Vitam. Nutr. Res., 1988, pp. 418-421, vol. 58, No. 4.

Roberfroid, M., Dietary Fiber, Inulin, and Oligofructose: A Review Comparing Their Physiological Effects, Crit. Rev. Food Sci., 1993, pp. 103-148, vol. 33, No. 2.

Rocha, et al., Fucan from the Brown Seaweed *Spatoglossum schroederi* Inhibits Chinese Hamster Ovary Cell Adhesive to Several Extracellular Matrix Proteins, Braz. J. Med. Biol. Res., 2001, pp. 621-626, vol. 34, No. 5.

Shier, et al., Hyaluronate, Tetrachlorodecaoxide, and Galactolipid Prevent Adhesions after Implantation of Gore-Tex and Dura Mater into the Abdominal Wall in Rats, Pediatr. Surg. Int., 1999, pp. 255-259, vol. 15, No. 3-4.

Sharon, et al., Safe as Mother's Milk: Carbohydrates as Future Anti-Adhesion Drugs for Bacterial Diseases, Glycoconj. J., 2000, pp. 659-664, vol. 17, No. 7-9.

Simon, et al., The Human Intestinal Microflora, Dig. Dis. Sci., 1986, pp. 147s-162s, vol. 31, No. 9 Suppl.

Tronchin, et al., Fungal Cell Adhesion Molecules in *Candida albicans*, European J. of Epidemiology, 1991, pp. 23-33, vol. 7, No. 1.

Valdivia, et al., Flow Cytometry and Bacterial Pathogenesis, Current Opinion in Microbiology, 1998, pp. 359-363, vol. 1.

* cited by examiner

TISSUE PRODUCTS COMPRISING A CLEANSING COMPOSITION

BACKGROUND OF INVENTION

The present invention is directed to cleansing compositions which may be used in combination with tissue products such as bath and facial tissue. More particularly, the present invention is directed to novel cleansing compositions for use on one or both surfaces of a tissue product, which improve the level of cleaning and comfort to the user, and may further provide a skin health benefit.

The skin is the largest organ of the human body. As a boundary layer, the skin performs several major functions: it maintains the body at a correct temperature, holds in essential fluids, and protects against toxic agents, microorganisms, and the sun's potentially harmful rays. Proper skin maintenance is essential for good health. For most people, proper skin maintenance begins with daily cleansing.

Human skin is exposed to, and soiled by, various contaminants daily through both contacts with various biological fluids, such as urine and feces, as well as contact with numerous environmental factors. Examples of contaminants that the skin contacts everyday include both Gram negative and Gram positive bacteria, yeast, fungi, mold, protozoan and viruses. Although most microbes are negatively charged due to their chemistry and structures, they can adhere to skin, which is also typically negatively charged, through electrostatic interactions, hydrophobic interactions and ligand interactions. Although these attachment mechanisms are not completely understood, their cumulative effect can tightly bind numerous microbes such as *Candida albicans* to skin resulting in inflammation, irritation and/or infection. Further, numerous other microbes, microbial metabolic products, and inorganic debris also contact and foul skin on a daily basis.

The above-listed contaminants, as well as numerous others, are often irritating to the skin and can initiate an elaborate cascade of immunological events upon contact with skin cells. Ultimately, these events may lead to severe skin irritation, inflammation, and even infection. Skin cleansing on a daily basis can prevent or minimize skin irritation and inflammation caused by the immunological events.

However, properly cleansing the skin can be difficult due to the skin's topography, the presence of hair follicles, and the sensitivity of the skin. Small amounts of soil can accumulate on the skin during daily activities. This soil may contain bacteria and active enzymes that irritate the skin and cause personal discomfort. Maintaining skin health through removal or repellence of microbes and soil is an important part of personal hygiene, especially in sensitive areas such as the perianal, uro-genital, and vaginal regions.

Based on the foregoing, there is a need for products, such as bath tissue or facial tissue, that can gently clean the skin without imparting substantial damage thereto due to abrasion and friction.

SUMMARY OF THE INVENTION

The present invention is generally directed to cleansing compositions for use in combination with tissue products such as bath and facial tissue. The cleansing compositions, which comprise a novel combination of a thermoplastic polymer or a thermosetting polymer and a water soluble neutral oligosaccharide, may be introduced onto one or both surfaces of a tissue product prior to contact with the skin. The cleansing compositions are capable of improving the health of skin they contact during normal usage by gently removing numerous bacteria, fungi, yeast, molds, protozoan, viruses, soils, and other substances from the skin's surface, without imparting substantial damage to the skin.

Briefly, therefore, the present invention is directed to a tissue product comprising a tissue paper and a cleansing composition. The cleansing composition comprises a thermoplastic polymer and a water soluble neutral oligosaccharide. The thermoplastic polymer is selected from the group consisting of polymethylmethacrylate, methyl methacrylate crosspolymer, polyethylene, ethylene/acrylate copolymer, Nylon_12, polymethylsilsesquioxane, ethylene vinyl alcohol, polyvinyl acetate, acrylic, polyvinyl acetate acrylate, acrylates, polyvinyl dichloride, ethylene vinyl acetate, ethylene vinyl chloride, polyvinyl chloride, styrene, styrene acrylate, styrene/butadiene, styrene/acrylonitrile, butadiene/acrylonitrile, acrylonitrile/butadiene/styrene, ethylene acylic acid, polyethylene, urethanes, polycarbonate, polypropylene, polyesters, and polyimides, and silicone resin. The water soluble neutral oligosaccride is selected from the group consisting of starch, dextran, inulin, and xanthan.

The present invention is further directed to a tissue product comprising a tissue paper and a cleansing composition. The cleansing composition comprises polymethylmethacrylate and a water soluble starch.

The present invention is further directed to a cleansing composition comprising a thermoplastic polymer and a water soluble neutral oligosaccharide. The thermoplastic polymer is selected from the group consisting of polymethylmethacrylate, methyl methacrylate crosspolymer, polyethylene, ethylene/acrylate copolymer, Nylon_12, polymethylsilsesquioxane, ethylene vinyl alcohol, polyvinyl acetate, acrylic, polyvinyl acetate acrylate, acrylates, polyvinyl dichloride, ethylene vinyl acetate, ethylene vinyl chloride, polyvinyl chloride, styrene, styrene acrylate, styrene/butadiene, styrene/acrylonitrile, butadiene/acrylonitrile, acrylonitrile/butadiene/styrene, ethylene acylic acid, polyethylene, urethanes, polycarbonate, polypropylene, polyesters, and polyimides, and silicone resin. The water soluble neutral oligosacchride is selected from the group consisting of starch, dextran, inulin, and xanthan.

The present invention is further directed to a method for removing microbes and soil from the skin to improve skin health. The method comprises contacting a tissue paper with the skin's surface. The tissue paper comprises a cleansing composition comprising a thermoplastic polymer and a water soluble neutral oligosaccharide. The thermoplastic polymer is selected from the group consisting of polymethylmethacrylate, methyl methacrylate crosspolymer, polyethylene, ethylene/acrylate copolymer, Nylon_12, polymethylsisesquioxane, ethylene vinyl alcohol, polyvinyl acetate, acrylic, polyvinyl acetate acrylate, acrylates, polyvinyl dichloride, ethylene vinyl acetate, ethylene vinyl chloride, polyvinyl chloride, styrene, styrene acrylate, styrene/butadiene, styrene/acrylonitrile, butadiene/acrylonitrile, acrylonitrile/butadiene/styrene, ethylene acylic acid, polyethylene, urethanes, polycarbonate, polypropylene, polyesters, and polyimides, and silicone resin. The water soluble neutral oligosaccharide is selected from the group consisting of starch, dextran, inulin, and xanthan.

The present invention is further directed to a tissue product having a cleaning value as defined herein of greater than about 0.8 and a gentleness value as defined herein of less than about 1.05.

The present invention is further directed to a tissue product comprising a tissue paper and a cleansing composition. The cleansing composition comprises a thermosetting polymer and a water soluble neutral oligosaccharide. The thermosetting polymer is selected from the group consisting of epoxy, phenolic, bismaleimide, polyimide, melamine/formaldehyde, polyester, urethanes, urea, and urea/formaldehyde. The water soluble neutral oligosaccharide is selected from the group consisting of starch, dextran, inulin, and xanthan.

DETAILED DESCRIPTION OF THE PREFERRED EMBODIMENTS

In accordance with the present invention, it has been discovered that when at least one surface of a tissue product is treated with a cleansing composition including a thermoplastic polymer or a thermosetting polymer and a water soluble neutral oligosacchride, the skin can be effectively cleaned of soil and contaminants without substantial damage. Surprisingly, the cleansing composition has a low coefficient of friction as it contacts the skin such that skin abrasion is minimal, yet is capable of substantially cleaning the skin.

The present invention is generally described herein in relation to a tissue product. The cleansing compositions described herein are suitable for use on one or both surfaces of a tissue product. Suitable tissue products include, for example, bath tissue, facial tissue, disposable towels, napkins, hanks, and polyolefin wipes.

The tissue products of the present invention comprise a tissue substrate in combination with a cleansing composition. As used herein, tissue products are meant to include bath tissue, facial tissue, towels, hanks, napkins, polyolefin wipes and the like. The present invention is useful with tissue products and tissue paper in general, including but not limited to conventionally felt-pressed tissue paper; high bulk pattern densified tissue paper; and high bulk, uncompacted tissue paper. Tissue paper suitable for use with the cleansing compositions described herein can be of a homogenous or multi-layered construction, and tissue paper products made therefrom can be of a single-ply or multi-ply construction. The tissue paper desirably has a basis weight of between about 10 $g/m^2$ and about 65 $g/m^2$, and density of about 0.6 g/cc or less. More desirably, the basis weight will be about 40 $g/m^2$ or less and the density will be about 0.3 g/cc or less. Most desirably, the density will be between about 0.04 g/cc and about 0.2 g/cc. Unless otherwise specified, all amounts and weights relative to the paper are on a dry basis. Tensile strengths in the machine direction can be in the range of from about 100 to about 5,000 grams per inch of width. Tensile strengths in the cross-machine direction are in the range of from about 50 grams to about 2,500 grams per inch of width. Absorbency is typically from about 5 grams of water per gram of fiber to about 9 grams of water per gram of fiber.

Conventionally pressed tissue paper and methods for making such paper are well known in the art. Such paper is typically made by depositing a papermaking furnish on a foraminous forming wire, often referred to in the art as a Fourdrinier wire. Once the furnish is deposited on the forming wire, it is referred to as a web. The web is dewatered by pressing the web and drying at elevated temperatures. The particular techniques and typical equipment for making webs according to the process just described are well known to those skilled in the art. In a typical process, a low consistency pulp furnish is provided from a pressurized headbox, which has an opening for delivering a thin deposit of pulp furnish onto the Fourdrinier wire to form a wet web.

The web is then typically dewatered to a fiber consistency of between about 7% and about 25% (total web weight basis) by vacuum dewatering and further dried by pressing operations wherein the web is subjected to pressure developed by opposing mechanical members, for example, cylindrical rolls. The dewatered web is then further pressed and dried by a steam drum apparatus known in the art as a Yankee dryer. Pressure can be developed at the Yankee dryer by mechanical means such as an opposing cylindrical drum pressing against the web. Multiple Yankee dryer drums can be employed, whereby additional pressing is optionally incurred between the drums. The formed sheets are considered to be compacted since the entire web is subjected to substantial mechanical compressional forces while the fibers are moist and are then dried while in a compressed state.

High bulk pattern densified tissue paper is characterized by having a relatively high bulk field of relatively low fiber density and an array of densified zones of relatively high fiber density. The high bulk field is alternatively characterized as a field of pillow regions. The densified zones are alternatively referred to as knuckle regions. The densified zones can be discretely spaced within the high bulk field or can be interconnected, either fully or partially, within the high bulk field. The patterns can be formed in a non-ornamental configuration or can be formed so as to provide an ornamental design(s) in the tissue paper. Preferred processes for making pattern densified tissue webs are disclosed in U.S. Pat. No. 3,301,746 (Sanford et al.), issued Jan. 31, 1967; U.S. Pat. No. 3,974,025 (Ayers), issued Aug. 10, 1976; and U.S. Pat. No. 4,191,609 (Trokhan), issued Mar. 4, 1980; and U.S. Pat. No. 4,637,859 (Trokhan), issued Jan. 20, 1987; all of which are incorporated by reference.

In general, pattern densified webs are preferably prepared by depositing a papermaking furnish on a foraminous forming wire such as a Fourdrinier wire to form a wet web and then juxtaposing the web against an array of supports. The web is pressed against the array of supports, thereby resulting in densified zones in the web at the locations geographically corresponding to the points of contact between the array of supports and the wet web. The remainder of the web not compressed during this operation is referred to as the high bulk field. This high bulk field can be further de-densified by application of fluid pressure, such as with a vacuum type device or a blow-through dryer, or by mechanically pressing the web against the array of supports. The web is dewatered, and optionally predried, in such a manner so as to substantially avoid compression of the high bulk field. This is preferably accomplished by fluid pressure, such as with a vacuum type device or blow-through dryer, or alternately by mechanically pressing the web against an array of supports wherein the high bulk field is not compressed. The operations of dewatering, optional predrying and formation of the densified zones can be integrated or partially integrated to reduce the total number of processing steps performed. Subsequent to formation of the densified zones, dewatering, and optional predrying, the web is dried to completion, preferably still avoiding mechanical pressing. Preferably, from about 8% to about 55% of the tissue paper surface comprises densified knuckles having a relative density of at least 125% of the density of the high bulk field.

Desirably, the furnish is first formed into a wet web on a foraminous forming carrier, such as a Fourdrinier wire. The web is dewatered and transferred to an imprinting fabric. The furnish can alternately be initially deposited on a foraminous supporting carrier that also operates as an imprinting fabric. Once formed, the wet web is dewatered and, preferably, thermally pre-dried to a selected fiber consistency from about 40% to about 80%. Dewatering is preferably performed with suction boxes or other vacuum devices or with blow-through dryers. The knuckle imprint of the imprinting fabric is impressed in the web as discussed above, prior to drying the web to completion. One method for accomplishing this is through application of mechanical pressure. This can be done, for example, by pressing a nip roll that supports the imprinting fabric against the face of a drying drum, such as a Yankee dryer, wherein the web is disposed between the nip roll and drying drum. Also, preferably, the web is molded against the imprinting fabric prior to completion of drying by application of fluid pressure with a vacuum device such as a suction box, or with a blow-through dryer. Fluid pressure can be applied to induce impression of densified zones during initial dewatering, in a separate, subsequent process stage, or a combination thereof.

Uncompacted, nonpattern-densified tissue paper structures are described in U.S. Pat. No. 3,812,000 (Salvucci et al.), issued May 21, 1974 and U.S. Pat. No. 4,208,459 (Becker et al.), issued Jun. 17, 1980, both of which are incorporated by reference. In general, uncompacted, non-pattern-densified tissue paper structures are prepared by depositing a papermaking furnish on a foraminous forming wire such as a Fourdrinier wire to form a wet web, draining the web and removing additional water without mechanical compression until the web has a fiber consistency of at least about 80%, and creping the web. Water is removed from the web by vacuum dewatering and thermal drying. The resulting structure is a soft but weak, high bulk sheet of relatively uncompacted fibers. Bonding material is preferably applied to portions of the web prior to creping.

Compacted non-pattern-densified tissue structures are commonly known in the art as conventional tissue structures. In general, compacted, non-pattern-densified tissue paper structures are prepared by depositing a papermaking furnish on a foraminous wire such as a Fourdrinier wire to form a wet web, draining the web and removing additional water with the aid of a uniform mechanical compaction (pressing) until the web has a consistency of 25-50%, transferring the web to a thermal dryer such as a Yankee and creping the web. Overall, water is removed from the web by vacuum, mechanical pressing and thermal means. The resulting structure is strong and generally of singular density, but very low in bulk, absorbency and softness.

The papermaking fibers utilized in preparing tissue paper for the products of the present invention will normally include fibers derived from wood pulp. Other cellulosic fibrous pulp fibers, such as cotton linters, bagasse, etc., can be utilized and are intended to be within the scope of this invention. Synthetic fibers, such as rayon, polyethylene and polypropylene fibers, can also be utilized in combination with natural cellulosic fibers. One exemplary polyethylene fiber that can be utilized is Pulpex.RTM, available from Hercules, Inc. (Wilmington, Del.).

Applicable wood pulps include chemical pulps, such as Kraft, sulfite, and sulfate pulps, as well as mechanical pulps including, for example, groundwood, thermo-mechanical pulp and chemically modified thermo-mechanical pulp. Chemical pulps, however, are typically desirable since they impart a superior tactile sense of softness to tissue sheets made therefrom. Pulps derived from both deciduous trees and coniferous trees can be utilized. Also useful in the present invention are fibers derived from recycled paper, which can contain any or all of the above categories as well as other non-fibrous materials such as fillers and adhesives used to facilitate the original papermaking.

In addition to papermaking fibers, the papermaking furnish used to make tissue paper structures can have other components or materials added thereto as can be or later become known in the art. The types of additives desirable will be dependent upon the particular end use of the tissue sheet contemplated. For example, in products such as bath tissue, paper towels, facial tissues and other similar products, high wet strength is a desirable attribute. Thus, it is often desirable to add to the papermaking furnish chemical substances known in the art as "wet strength" additives.

In addition to wet strength additives, it can also be desirable to include in the papermaking fibers certain dry strength and lint control additives known in the art. In this regard, starch binders have been found to be particularly suitable. In addition to reducing tinting of the finished tissue paper product, low levels of starch binders also impart a modest improvement in the dry tensile strength without imparting stiffness that could result from the addition of high levels of starch. Typically, the starch binder is included in an amount such that it is retained at a level of from about 0.01 to about 2%, preferably from about 0.1 to about 1%, by weight of the dry tissue paper.

The cleansing formulations described herein for use in combination with the tissue product are either solid or semi-solid at room temperature. As used herein, the term "semi-solid" means that the cleansing formulation has a rheology typical of pseudoplastic or plastic fluids. When applied to the tissue product, the cleansing formulations described herein impart a soft, lubricious, lotion-like feel to the touch. The cleansing formulation gently removes microbes and soils upon use to improve the skin health of the user.

The tissue product includes a cleansing composition as described herein on at least one surface thereon. The cleansing composition provides a cleaning function on the skin's surface, while being gentle and substantially non-abrasive to the skin. As used herein, the term "gentle" means that the cleansing composition does not cause substantial damage to the stratum corneum layer of the skin upon use, and is minimally abrasive to the skin's surface. As noted above, in one embodiment, the cleansing compositions of the present invention for use in combination with a tissue product comprise a thermoplastic polymer. As used herein, the term "thermoplastic polymer" refers to a material that softens when exposed to heat and which substantially returns to a non-softened condition when cooled to room temperature. These compounds can be re-melted and cooled several times without undergoing any appreciable chemical change or deterioration.

Thermoplastic polymers suitable for use in the cleansing compositions described herein include both thermoplastic powders and thermoplastic resins which are insoluble in oils. These thermoplastic powders and thermoplastic resins are suitably insoluble in the oily soils and aqueous soils typically present on the surface of the skin. As such, they tend to impart a feeling of silkiness, smoothness, and softness to the user's skin upon use. The thermoplastic polymer may provide a ball bearing-type effect on the skin's surface, which further imparts elegant feel and enhanced slip without substantial damage to the skin's surface.

The cleansing compositions of the present invention comprise from about 10% (by total weight of the cleansing composition) to about 90% (by total weight of the cleansing composition) of the thermoplastic polymer. As used herein, the term "by total weight of the cleansing composition" refers to the total weight of the cleansing composition, including all components thereof. For example, if the cleansing composition comprises 25% (by total weight of the cleansing composition) of thermoplastic polymer and has a total weight including all components of 100 grams, the composition comprises 25 grams of thermoplastic polymer.

The thermoplastic polymers included in the cleansing compositions may suitably be in the form of a spherical powder or spherical resin. To provide the intended benefits of the present invention, the thermoplastic polymers suitably have an average particle diameter of from about 0.1 micrometers to about 20 micrometers, and suitably from about 0.1 micrometers to about 12 micrometers, and even more suitably from about 0.4 micrometers to about 7 micrometers. Within these ranges, the thermoplastic polymers may provide both a cleaning and gentleness function.

Specifically, suitable thermoplastic polymers for use in the cleansing composition include, but are not limited to, polymethylmethacrylate, available as MP-2200, ES-830, and BPA-500 manufactured by KOBO Products, Inc. (South Plainfield, N.J.), methyl methacrylate crosspolymer manufactured by KOBO (South Plainfield, N.J.), polyethylene, available as CL-2080 manufactured by KOBO (South Plainfield, N.J.), ethylene/acrylate copolymer, available as EA-209 manufactured by KOBO (South Plainfield, N.J.), Nylon__12, available as SP-500 and SP-501 manufactured by KOBO (South Plainfield, N.J.), polymethylsilsesquioxane manufactured by KOBO (South Plainfield, N.J.), ethylene vinyl alcohol, polyvinyl acetate, acrylic, polyvinyl acetate acrylate, acrylates, polyvinyl dichloride, ethylene vinyl acetate, ethylene vinyl chloride, polyvinyl chloride, styrene, styrene acrylate, styrene/butadiene, styrene/acrylonitrile, butadiene/acrylonitrile, acrylonitrile/butadiene/styrene, ethylene acylic acid, polyethylene, urethanes, polycarbonate, polypropylene, polyesters, polyimides, and silicone resins. Particularly preferred thermoplastic polymers include polymethylmethacrylates and methyl methacrylate crosspolymers.

Suitable silicone resins are characterized by their three-dimensional structure having a siloxane-linked backbone. Suitable silicone resins include TP-120A, TP-145A, and TP-2000B, manufactured by KOBO, as well as KMP-590 and KMP-599 manufactured by Shin-Etsu Co., Ltd. (Tokyo, Japan). Silicone resins suitable for use in the cleansing compositions are mixtures of toluene or xylene solvents with combined hydrolyzates of methyl chlorosilanes and phenyl chlorosilanes containing hydroxyl groups.

In one embodiment of the present invention, the cleansing composition includes as the thermoplastic polymer component a spherically shaped polymethylmethacrylate powder. Suitably, the spherical shaped polymethylmethacrylate powder has an average particle diameter of from about 0.1 micrometers to about 20 micrometers, more suitably, from about 0.1 micrometers to about 12 micrometers, and even more suitably, from about 0.4 micrometers to about 7 micrometers.

As noted above, the cleansing compositions additionally include a water soluble neutral oligosacchride. The water soluble neutral oligosaccharide component of the cleansing composition is generally present in an amount of from about 10% (by total weight of the cleansing composition) to about 90% (by total weight of the cleansing composition). Suitable water soluble neutral oligosaccharides for inclusion in the cleansing compositions of the present invention include, but are not limited to, starches, dextrans, inulins, and xanthans.

Suitable starches include those derived from sources including corn starch, potato starch, arrowroot starch, rice starch, sorghum gum, and tapioca starch. Suitably, the starch for inclusion in the cleansing composition may be a high molecular-weight, water soluble starch. As used herein, the term "high molecular weight" refers to a molecular weight of at least about 0.5 kilodaltons, and suitably from about 0.5 kilodaltons to about 1000 kilodaltons or more.

In one suitable embodiment, the high molecular-weight, water soluble starch is a high molecular-weight, water soluble dextrin. Even more suitably, the high molecular-weight, water soluble starch is amylodextrin. Amylodextrin is a specific high molecular-weight (about 25 kilodaltons), water soluble dextrin produced by the partial acid hydrolysis of starch.

In one embodiment of the present invention, the cleansing compositions described herein comprise the thermoplastic polymer and the water soluble neutral oligosacchride in a weight ratio of from about 1:9 to about 9:1 respectively. In a desired embodiment, the weight ratio is from about 6:1 to about 9:1 thermoplastic polymer to water soluble neutral oligosaccharide.

Without being bound to a particular theory, it appears that the cleansing compositions of the present invention provide for improved cleansing of the skin by affecting the static coefficients of friction, or the frictional force required to break the adhesion of contaminants, such as microbes or soil, from the surface of the skin. A high static coefficient of friction imparts an abrasive feeling to the skin; whereas a lower static coefficient of friction imparts gentleness. The cleansing compositions provide for static coefficients of friction which, while allowing for sufficient cleaning, are suitably non-abrasive to the skin's surface.

Additionally, it appears that the thermoplastic polymers, such as polymethylmethacrylate, impart a somewhat higher coefficient of friction, providing a somewhat abrasive effect to the user's skin. This allows for improved cleansing of the skin. The water soluble neutral oligosaccharide, such as water soluble starch, provides a mitigating effect to the abrasiveness of the thermoplastic polymer, thereby allowing for a more gentle cleansing composition. Therefore, the cleansing composition of the present invention is capable of providing improved skin health by improving the level of cleansing while remaining gentle on the user's skin.

In another embodiment of the present invention, the cleansing composition comprises a thermosetting polymer and a water soluble neutral oligosaccharide. As used herein, the term "thermosetting polymer" refers to a material that becomes permanently hard and rigid when heated or cured. Therefore, once reacted, thermosetting polymers cannot be remelted or remolded without substantially destroying their original molecular characteristics. Thermosetting polymers suitable for use in the cleansing composition include both thermosetting powders and thermosetting resins.

The cleansing compositions of the present invention may comprise from about 1% (by total weight of the cleansing composition) to about 40% (by total weight of the cleansing composition) of the thermosetting polymer.

Suitable thermosetting polymers for use in the cleansing composition include, but are not limited to, epoxy, phenolic, bismaleimide, polyimide, melamine/formaldehyde, polyester, urethanes, urea, and urea/formaldehyde.

In some cleansing compositions described herein, the thermosetting polymer and the water soluble neutral oligosaccharide are present at a weight ratio of from about 1:9 to about 9:1 respectively. In a desired embodiment, the weight ratio is from about 6:1 to about 9:1 thermosetting polymer to water soluble neutral oligosaccharide.

The cleansing compositions of the present invention may also optionally include other components such as emulsifiers, surfactants, water, viscosity modifiers, pH modifiers, buffers, enzyme inhibitors/inactivators, suspending agents, natural moisturizing factors, humectants, moisturizer, microencapsulated skin health benefit agents, emollients, pigments, dyes, colorants, perfumes, antibacterial actives, antifungal actives, pharmaceutical actives, film formers, deodorants, opacifiers, astringents, solvents, organic acids, coloring agents, preservatives, antivirul actives, drugs, vitamins, aloe vera, panthenol, and the like. These materials are known in the art and are used in their art-established manner at their art-established amounts.

The cleansing compositions of the present invention are introduced onto one or both surfaces of a tissue paper in an amount sufficient to provide a cleansing benefit in a gentle manner. For example, the cleansing compositions of the present invention may be introduced onto one or both surfaces of a tissue paper in an amount of from about 0.01% (by weight of the tissue paper) to about 25% (by weight of the tissue paper), more suitably from about 1% (by weight of the tissue paper) to about 5% (by weight of the tissue paper), and more suitably from about 1% (by weight of the tissue paper) to about 2% (by weight of the tissue paper).

In another embodiment of the present invention, the tissue products described herein comprise a cleansing compound such that they have a specific cleaning value in combination with a specific gentleness value. The cleaning value and gentleness value of a specific tissue product may be determined utilizing the procedures set forth in the Examples disclosed herein. Specifically, it is desirable for a tissue product comprising the cleansing compositions described herein to have a cleaning value of greater than about 0.8, suitably greater than about 1.0 in combination with a gentleness value of less than about 1.05 and suitably less than about 1.0.

As described in the Examples, both the cleaning value and the gentleness value are measured and referenced to a standard. The better a tissue product cleans, the higher the cleaning value, whereas the more gentle the tissue, the lower the gentleness value. By requiring a tissue product to have both a required cleaning value and a required gentleness value, superior tissue products are delivered as the tissue product is a highly effective skin cleaning agent, yet gentle on the outer layers of the skin such that abrasive damage is not imparted.

The present invention is illustrated by the following Examples, which are not meant to be limiting in any manner.

EXAMPLE 1

In this Example, neat bath tissue and bath tissue comprising various cleansing compositions (referred to hereafter as "test tissues") were tested to determine their gentleness on a human skin simulant. Gentleness on the skin was determined by the ratio of the static coefficient of friction of the test tissue to the static coefficient of friction of a corduroy control substrate.

Each tissue tested was cut into 6 centimeters by 8 centimeters sections with the 8 centimeters side parallel to the perforations on the tissue. The tissue was then allowed to equilibrate in a controlled environment at 23° C. and 50% relative humidity for at least four hours prior to use.

Vitro Skin™ N19-5X (IMS, Milford, Conn.) was used as a skin simulant. The Vitro Skin™ was cut into 4 centimeters by 13.5 centimeters pieces and allowed to hydrate for 20 hours in a hydration chamber. The hydration chamber consisted of a large Tupperware container (35 centimeters by 24 centimeters by 12 centimeters) filled with 500 milliliters of a 30% glycerol, available from Sigma (St. Louis, Mo.) and water solution. The hydration chamber was placed in a controlled environment with a temperature of 23° C. and 50% relative humidity.

A monitor/slip and friction instrument, available as Model 32-06 from TMI (Amityville, N.Y.) was used. to conduct frictional force measurements. The slip and friction instrument was calibrated before every use as specified by the manufacturer. A modified sled was custom made to have a bottom surface area of 5 centimeters by 3 centimeters and a weight of 73 grams. The slip and friction instrument was set to move the sled at a rate of 38.1 centimeters/minute, and to stop after traveling 8.25 centimeters. A 1000-gram weight was placed on the sled before testing began to add extra weight. The normal force was set at 1074 grams to account for the sled, the 1000-gram weight, test tissue samples and clips. The forward velocity of the sled was set at 15 inches/minute.

All tests were performed in an environmentally controlled room having a temperature of 23° C. and 50% relative humidity. All dry cleansing compositions to be tested were applied to the bath tissue by placing 20 grams of the cleansing compositions in a plastic ziplock bag. Six cut sheets of Cottonelle bath tissue were introduced into the bag. The bag was then vigorously shaken. The materials, along with the compositions used, are listed in Table 1.

TABLE 1

| Material | Composition to be Tested | Supplier of Composition |
| --- | --- | --- |
| Cottonelle* | 20 g Polymethylmethacrylate (PMMA) per mix bag | MP-2200, KOBO Products, Inc. (South Plainfield, NJ) |
| Cottonelle | NONE | N/A |
| Cottonelle | 20 g DRYFLOW LL Insoluble Starch per mix bag | National Starch and Chemical Co. (Bridgewater, NJ) |
| Cottonelle | 20 g DRYFLOW BN Insoluble Starch per mix bag | National Starch and Chemical Co. (Bridgewater, NJ) |
| Cottonelle | 18 g PMMA + 2 g Soluble Sigma Starch (S-4126) per mix bag (9:1 PMMA:Soluble Starch) | Sigma (St. Louis, MO) |
| Cottonelle | 20 g Soluble Sigma Starch (S-4126) per mix bag | Sigma (St. Louis, MO) |
| Cottonelle A&E** | None | N/A |
| Cottonelle | 20 g Nylon Beads per mix bag | Nylon 12, SP-501, KOBO (batch 01004) |
| Cottonelle | 18 g Soluble Sigma Starch (S-4126) + 2 g PMMA per mix bag (9:1 Soluble Starch:PMMA) | Sigma (St. Louis, MO) |

*Cottonelle is commercially available bath tissue from Kimberly-Clark Worldwide, Inc.
**Cottonelle A&E is commercially available bath tissue from Kimberly-Clark Worldwide, Inc.

After the shaking was discontinued, one coated test tissue sheet was removed. Coating ranged from about 5 milligrams to about 10 milligrams per cut sheet of test tissue. The test tissue was clipped to the lip of the sled using three mini-binder clips, available from EXP (Broomfield, Colo.); one clip at the top and one clip on each side. The finger grips of the clips were bent up so they did not touch the Vitro Skin™ during testing.

A piece of Vitro Skin™ was placed on the shiny of a 5 centimeters by 15 centimeters piece of silicone skin, available from SiliClone (Valley Forge, Pa.), and was secured to the instrument with the slip and friction instrument sample retaining clip. The edge of the Vitro Skin™ was secured with the same clip. The sled, with the test tissue attached, was placed into its position on the instrument and lined up over the Vitro Skin™. A new piece of Vitro Skin™ and test tissue was used for each test, and one wipe was conducted per test.

In order to assure consistency of the slip and friction instrument from day to day, a corduroy material, available as Cotton 16 Wale Corduroy, style 411, manufactured by Test Fabrics (West Pittston, Pa.) was designated as the control material and was tested each day on the instrument. The average static coefficient of friction value of the control material was compared to the static coefficient of friction values from previous days to ensure there was no statistical difference.

Each test tissue was tested six times and the static coefficient of friction for each test tissue was averaged. Differences between the test tissues were determined by using ANOVA analysis of variance on the static coefficient of friction values.

Gentleness of the test tissues was determined by dividing the static coefficient of friction of the test tissue, or the force required to start the tissue moving, by the static coefficient of friction of the corduroy control. A gentler cleansing composition will result in a lower gentleness value. As noted in Table 2, the tissues containing 9:1 Soluble Starch:PMMA resulted in the lowest gentleness value, 0.775, which corresponds with the gentlest composition.

TABLE 2

| Composition | Gentleness Value | Standard Deviation |
|---|---|---|
| PMMA | 1.095 | 0.043 |
| Cottonelle Neat | 1.076 | 0.083 |
| DRYFLO_LL | 0.991 | 0.071 |
| DRYFLO_BN | 0.887 | 0.066 |
| 9:1 PMMA:Soluble Sigma Starch | 0.863 | 0.070 |
| Soluble Sigma Starch | 0.862 | 0.052 |
| Cottonelle A&E Neat | 0.847 | 0.039 |
| Nylon_12 | 0.805 | 0.037 |
| 9:1 Soluble Sigma Starch:PMMA | 0.775 | 0.043 |

Gentleness Value = Static Coefficient of Friction of Test Material/Static Coefficient of Friction of Corduroy Control

EXAMPLE 2

In this Example, neat bath tissue and bath tissue comprising various cleansing compositions (referred to hereafter as "test tissues") were tested to determine their ability to effectively clean a human skin simulant. Cleaning effectiveness was determined by comparing the cleaning performance of the test tissue with the cleaning performance of an unwiped Vitro-Corneum™ piece, the control.

Each test tissue was cut into 13 centimeters by 5 centimeters pieces. The test tissue was then allowed to equilibrate in a controlled environment at 23° C. and 50% relative humidity for at least four hours prior to use.

Vitro-Corneum™ (IMS, Milford, Conn.) was used as a skin simulant. The Vitro-Corneum™ was cut into 5 centimeters by 5 centimeters pieces. 20 microliters of 10-micrometer carboxylate-modified fluorescent beads, available from Bangs Laboratories, Inc. (Fishers, Ind.) were applied to each piece of Vitro-Corneum™, and the pieces were then allowed to hydrate overnight in a hydration chamber. The hydration chamber consisted of a large Tupperware container (35 centimeters by 24 centimeters by 12 centimeters) filled with 500 milliliters of a 30% glycerol, available from Sigma (St. Louis, Mo.) and water solution. The hydration chamber was placed in a controlled environment of a temperature of 23° C. and 50% relative humidity.

All tests were performed in an environmentally controlled room having a temperature of 23° C. and 50% relative humidity. All dry cleansing compositions to be tested were applied to the bath tissue by placing 20 grams of the cleansing mixtures in a plastic ziplock bag. Six cut sheets of Cottonelle bath tissue were introduced into the bag. The bag was then vigorously shaken. The materials, along with the compositions used, are listed in Table 3.

TABLE 3

| Material | Composition to be Tested | Supplier of Composition |
|---|---|---|
| Cottonelle | 20 g PMMA per mix bag | MP-2200, KOBO Products, Inc. |
| Cottonelle | None | N/A |
| Cottonelle | 18 g PMMA + 2 g Sigma Starch (S-4126) per mix bag (9:1 PMMA:Soluble Starch) | Sigma (St. Louis, MO) |
| Cottonelle | 20 g Soluble Sigma Starch (S-4126) per mix bag | Sigma (St. Louis, MO) |
| Cottonelle A&E | None | N/A |
| Cottonelle | 18 g Soluble Sigma Starch (S-4126) + 2 g PMMA per mix bag (9:1 Soluble Starch:PMMA) | Sigma (St. Louis, MO) |

After the shaking was discontinued, one coated test tissue sheet was removed. Coating ranged from about 5 milligrams to about 10 milligrams per cut sheet of test tissue.

The test tissue was loaded onto the Cleaning Efficiency Measurement System I (CEM I) wiping instrument, available from Kimberly-Clark (Neenah, Wis.). The CEM I was developed to evaluate the wiping characteristics of tissue and bath products. The instrument consists of a moving horizontal bed to contain test fluids and substrates. A probe capable of holding test tissues was suspended above the horizontal bed.

One piece of Vitro-Corneum™ was secured onto the horizontal bed of the CEM I using tape. The CEM I probe was then lowered to the horizontal bed. The CEM I was moved by a variable speed DC motor and slide wire assembly to create a wiping motion. All test tissue samples were tested by wiping in the cross direction, with the fabric side in contact with the Vitro-Corneum™. Cottonelle® Rollwipes were tested wiping in the machine direction.

The Vitro-Corneum™ was wiped once with the material to be examined. If repetitive wiping was needed, each wipe was performed with a fresh piece of test tissue. The Vitro-Corneum™ pieces and/or the test tissues were placed into a 50-mililiters conical tube. 20 mililiters of 0.25% sodium dodecyl sulfate, available from Sigma (St. Louis, Mo.) was added to each tube. The beads were extracted from each sample using a VirSonic™ microtip probe sonicator (Gardiner, N.Y.). Three 2-mililiters samples were withdrawn from each 50-mililiters conical tube and placed into 5-mililiters tubes for flow cytometry analysis using a FACSCalibur™ flow cytometer, available from Becton Dickinson Biosciences (San Jose, Calif.). Using CellQuest software, available from Becton Dickinson Biosciences, the acquired data was analyzed and the desired bead population was counted.

To compare test materials, a cleaning value was calculated by dividing the number of beads acquired by the test tissue by the number of beads acquired by the control, an unwiped Vitro-Corneum™ piece with beads applied and extracted using the sonication method described above. A higher cleaning value corresponds to a better cleansing composition. The tissues containing 9:1 PMMA:Soluble Starch resulted in the highest cleaning value, 1.210, which corresponds with the best cleansing composition. These results are shown in Table 4.

TABLE 4

| Composition | Cleaning Value | Standard Deviation |
|---|---|---|
| 9:1 PMMA:Soluble Sigma Starch | 1.210 | 0.217 |
| PMMA | 0.852 | 0.457 |
| 9:1 Soluble Sigma Starch:PMMA | 0.792 | 0.530 |
| Cottonelle | 0.790 | 0.298 |
| Soluble Sigma Starch | 0.723 | 0.353 |
| Cottonelle A&E | 0.738 | 0.279 |

Cleaning Value = Number of beads acquired by the test tissue/Number of beads acquired by the control In view of the above, it will be seen that the several objects of the invention are achieved. As various changes could be made in the above-described products and methods without departing from the scope of the invention, it is intended that all matter contained in the above description be interpreted as illustrative and not in a limiting sense.

What is claimed is:

1. A tissue product for improving skin health comprising a tissue paper and a cleansing composition, the cleansing composition comprising a thermoplastic polymer and a water soluble neutral oligosaccharide, wherein the thermoplastic polymer is selected from the group consisting of polymethylmethacrylate, methyl methacrylate crosspolymer, polyethylene, ethylene/acrylate copolymer, Nylon__12, polymethylsilsesquiosane, ethylene vinyl alcohol, polyvinyl acetate, acrylic, polyvinyl acetate acrylate, acrylates, polyvinyl dichloride, ethylene vinyl acetate, ethylene vinyl chloride, polyvinyl chloride, styrene, styrene acrylate, polymethylsilsesquiosanestyrene/butadiene, styrene/acrylonitrile, butadiene/acrylonitrile, acrylonitrile/butadiene/styrene, ethylene acylic acid, polyethylene, urethanes, polycarbonate, polypropylene, polyesters, polyimides, and silicone resin, and wherein the water soluble neutral oligosaccharide is a water soluble starch.

2. The tissue product as set forth in claim 1 wherein the thermoplastic polymer is polymethylmethacrylate.

3. The tissue product as set forth in claim 1 wherein the starch has a molecular-weight of from about 0.5 kilodaltons to about 1000 kilodaltons.

4. The tissue product as set forth in claim 1 wherein the starch is a high molecular-weight, water soluble dextrin.

5. The tissue product as set forth in claim 1 wherein the starch is amylodextrin.

6. The tissue product as set forth in claim 1 wherein the starch is derived from a source selected from the group consisting of corn starch, arrowroot starch, rice starch, sorghum gum, and tapioca starch.

7. The tissue product as set forth in claim 1 wherein the thermoplastic polymer is a spherical powder or resin.

8. The tissue product as set forth in claim 1 wherein the thermoplastic polymer has an average particle diameter of from about 0.1 micrometers to about 20 micrometers.

9. The tissue product as set forth in claim 1 wherein the thermoplastic polymer has an average particle diameter of from about 0.1 micrometers to about 12 micrometers.

10. The tissue product as set forth in claim 1 wherein the thermoplastic polymer has an average particle diameter of from about 0.4 micrometers to about 7 micrometers.

11. The tissue product as set forth in claim 1 wherein the cleansing composition comprises from about 10% (by total weight of the cleansing composition) to about 90% (by total weight of the cleansing composition) of the thermoplastic polymer and from about 10% (by total weight of the cleansing composition) to about 90% (by total weight of the cleansing composition) of the water soluble neutral oligosaccharide.

12. The tissue product as set forth in claim 1 wherein the cleansing composition comprises a weight ratio of thermoplastic polymer to water soluble neutral oligosaccharide of about 9:1.

13. The tissue product as set forth in claim 1 wherein the cleansing composition comprises a weight ratio of thermoplastic polymer to water soluble neutral oligosaccharide of about 1:9.

14. The tissue product as set forth in claim 1 wherein the cleansing composition is present in an amount from about 0.01% (by weight of the tissue paper) to about 25% (by weight of the tissue paper).

15. The tissue product as set forth in claim 1 wherein the cleansing composition is present in an amount of from about 1% (by weight of the tissue paper) to about 5% (by weight of the tissue paper).

16. The tissue product as set forth in claim 1 wherein the cleansing composition is present in an amount of from about 1% (by weight of the tissue paper) to about 2% (by weight of the tissue paper).

17. The tissue product as set forth in claim 1 wherein the tissue paper is selected from the group consisting of bath tissue, facial tissue, disposable towels, napkins, hanks, and polyolefin wipes.

18. The tissue product as set forth in claim 1 wherein the cleansing composition comprises at least one additional component selected from the group consisting of emulsifiers, surfactants, humectants, moisturizers, emollients, microencapsulated skin health actives, water, viscosity modifiers, pH modifiers, buffers, enzyme inhibitors/inactivators, suspending agents, natural moisturizing actives, antifungal actives, pharmaceutical actives, film formers, deodorants, opacifiers, astringents, solvents, organic acids, coloring agents, preservatives, antivirul actives, drugs, vitamins, aloe vera, panthenol, and combinations thereof.

19. A tissue product for improving skin health comprising a tissue paper and a cleansing composition, wherein the cleansing composition comprises polymethylmethacrylate and a water soluble starch.

20. The tissue product as set forth in claim 19 wherein the starch has a molecular-weight of from about 0.5 kilodaltons to about 1000 kilodaltons.

21. The tissue product as set forth in claim 19 wherein the starch is a high molecular-weight, water soluble dextrin.

22. The tissue product as set forth in claim 19 wherein the starch is amylodextrin.

23. The tissue product as set forth in claim 19 wherein the starch is derived from a source selected from the group consisting of potato starch, corn starch, arrowroot starch, rice starch, sorghum gum, and tapioca starch.

24. The tissue product as set forth in claim 19 wherein the polymethylmethacrylate is a spherical powder.

25. The tissue product as set forth in claim 24 wherein the polymethylmethacrylate powder has an average particle diameter of from about 0.1 micrometers to about 20 micrometers.

26. The tissue product as set forth in claim 24 wherein the polymethylmethacrylate powder has an average particle diameter of from about 0.1 micrometers to about 12 micrometers.

27. The tissue product as set forth in claim 24 wherein the polymethylmethacrylate powder has an average particle diameter of from about 0.4 micrometers to about 7 micrometers.

28. The tissue product as set forth in claim 19 wherein the cleansing composition comprises a weight ratio of polymethylmethacrylate to starch of about 9:1.

29. The tissue product as set forth in claim 19 wherein the gentle cleansing composition comprises a weight ratio of polymethylmethacrylate to starch of about 1:9.

30. The tissue product as set forth in claim 19 wherein the cleansing composition is present in an amount from about 0.01% (by weight of the tissue paper) to about 25% (by weight of the tissue paper).

31. The tissue product as set forth in claim 19 wherein the cleansing composition is present in an amount from about 1% (by weight of the tissue paper) to about 5% (by weight of the tissue paper).

32. The tissue product as set forth in claim 19 wherein the cleansing composition is present in an amount from about 1% (by weight of the tissue paper) to about 2% (by weight of the tissue paper).

33. The tissue product as set forth in claim 19 wherein the cleansing composition comprises from about 10% (by total weight of the cleansing composition) to about 90% (by total weight of the cleansing composition) of polymethylmethacrylate and from about 10% (by total weight of the cleansing composition) to about 90% (by total weight of the cleansing composition) of water soluble starch.

34. The tissue product as set forth in claim 19 wherein the tissue is selected from the group consisting of bath tissue, facial tissue, disposable towels, napkins, hanks, and polyolefin wipes.

35. The tissue product as set forth in claim 19 wherein the cleansing composition comprises at least one additional component selected from the group consisting of emulsifiers, surfactants, water, viscosity modifiers, pH modifiers, buffers, enzyme inhibitors/inactivators, suspending agents, natural moisturizing actives, humectants, moisturizers, emollients, encapsulated skin health ingredients, antifungal actives, pharmaceutical actives, film formers, deodorants, opacifiers, astringents, solvents, organic acids, coloring agents, preservatives, antivirul actives, drugs, vitamins, aloe vera, panthenol, and combinations thereof.

* * * * *